United States Patent [19]
Frost

[11] Patent Number: 5,621,985
[45] Date of Patent: Apr. 22, 1997

[54] JUMPING ASSIST SYSTEM

[76] Inventor: John H. Frost, 6900 Canby Ave - #110, Reseda, Calif. 91335

[21] Appl. No.: 538,117

[22] Filed: Oct. 2, 1995

Related U.S. Application Data

[60] Division of Ser. No. 280,226, Jul. 25, 1994, Pat. No. 5,475,935, which is a continuation-in-part of Ser. No. 80,823, Jun. 24, 1993, abandoned.

[51] Int. Cl.$^6$ .................. A43B 7/32; A61H 1/00
[52] U.S. Cl. .................. 36/89; 36/27; 36/1; 602/27
[58] Field of Search .................. 36/1, 89, 88, 91, 36/102, 132, 27, 28; 482/74, 77, 79, 51; 602/65, 27

[56] References Cited

U.S. PATENT DOCUMENTS

| | | | |
|---|---|---|---|
| 427,136 | 5/1890 | Walker | 482/77 |
| 979,243 | 12/1910 | Anderson | 482/51 |
| 1,374,669 | 4/1921 | McClellan | 602/65 |
| 4,294,238 | 10/1981 | Woodford | 482/79 |
| 4,941,273 | 7/1990 | Gross | 36/114 |
| 5,090,138 | 2/1992 | Borden | 36/102 |
| 5,125,171 | 6/1992 | Stewart | 36/89 |
| 5,224,925 | 7/1993 | Varn | 602/27 |
| 5,269,748 | 12/1993 | Lonardo | 602/27 |
| 5,431,624 | 7/1995 | Saxton et al. | 36/89 |
| 5,475,935 | 12/1995 | Frost | 36/89 |

Primary Examiner—Marie D. Patterson
Attorney, Agent, or Firm—Jack C. Munro

[57] ABSTRACT

A jumping assist system to be mounted in conjunction with each lower leg and foot of a human which will cause the imparting of additional energy during the jumping movement which will result in the individual being able to jump higher, especially in a succession of jumps, as well as having greater endurance in jumping. When the lower leg moves forwardly into the jump-ready position, a pulling force is applied from the lower leg to a tension brace which extends substantially parallel to the back of the leg to under the heel of the foot causing a forward rotational force at the ankle joint. This force will assist the individual in the jumping action. There is also a separate strap connection over the dorsum of the foot which extends along the bottom of the foot and under the heel, anchoring in the achilles area. This dorsum strap further assists in achieving an increased level of upward support and some rotational force that assists the individual in the jumping motion.

3 Claims, 2 Drawing Sheets

JUMPING ASSIST SYSTEM

REFERENCE TO PRIOR APPLICATION

This application is a divisional of patent application Ser. No. 08/280,226, filed Jul. 25, 1994, entitled JUMPING ASSIST SYSTEM, by the same inventor, now U.S. Pat. No. 5,475,935, which is a continuation in part of Ser. No. 08/080823, filed Jun. 24, 1993, now abandoned.

BACKGROUND OF THE INVENTION

1) Field of the Invention

The field of this invention relates to devices to assist a human in jumping and further to a system utilized in conjunction with each lower leg and foot of the human which will result in greater energy being obtained in the jumping motion.

2) Description of Prior Art

In the sport of basketball, players not only jump to significant heights, but are continually jumping as well as running over long periods of time. Regardless of their athletic ability, players will lose endurance in jumping as the basketball game is played.

Basketball shoes in the past have been designed to assist players in the jumping action. However, this assistance has been limited to the designing of the soles to be shock absorbing or to have a certain amount of elasticity so as to somewhat assist the jumper in the jumping action. However, this assistance has been relatively minimal. There has not been known, prior to the present invention, any device which takes into account certain movements of the leg and foot during the jumping action and connects to the human's leg and foot a device which increases the jumping force by harnessing the energy of those certain movements.

Within the prior art there have been attempts at designing springing devices in conjunction with shoes. One example of such a device is shown within U.S. Pat. No. 5,090,138, issued Feb. 25, 1992 to Robert Borden. In this patent to Borden there is shown a spring strap vertically connecting a shin brace and a heel socket. The shin brace and heel socket are connected by an ankle hinge axis. Borden's structure is highly dysfunctional for several reasons. In order for a force to move an object, the force must be independent of the object. One can't lift a box if one is standing on the box. Borden's shin brace 14 cannot lift heel socket 12 via spring strap 38 because the shin brace 14 is attached to the heel socket 12 at ankle hinge 16. The heel socket 12 and shin brace 14 are pulling on each other. A problem encountered by the current inventor is to maintain the shin brace in place. Bordon's shin brace 14 is held in place by the ankle hinge 16 so the ankle hinge 16 will likewise hold the heel socket 12 in place preventing any upward thrust.

Any rotational movement at ankle hinge 16 would also be unlikely because the human ankle joint not only rotates but moves forwardly as much as an inch when moving into the jump-ready position. That is, when the foot contacts the ground, the whole lower leg moves forwardly including the ankle joint and Achilles area, which is depicted incorrectly in FIG. 2 of Borden as though the leg were broken at the ankle or made of rubber. Borden has created a binding isosceles triangle with spring strap 38 as the base and ankle hinge point 16 the top. When the jumper's knee bends and the lower leg moves forwardly into the jump-ready position, the jumper's ankle joint at the ankle hinge 16 area also moves forwardly. Yet for a lengthening to occur at spring strap 38, ankle hinge 16 and spring strap 38 must move closer together as the triangle flattens. The reverse would occur when the jumper's foot moves into an obtuse angle at lift-off. The net result is the structure of Borden will bind up.

In the present invention, the jumper's foot is free to move independently of the force applied to it, and there is no binding problem. In the preferred embodiment, the force which propels the foot to lift-off position is supported by an angle brace which is in turn supported by the ground under the shoe, with no attachment or support to the angle brace from the upper leg. The converting of force from the forward motion of the human leg to upward motion of the heel occurs over a much larger distance than the stretching distance of Borden's spring strap, so there is far greater energy return. A leg strap is anchored at the shin area. As the jumper's leg bends at the knee causing the shin to move forward and further away from the heel, a tremendous force is exerted between the shin and the heel through a connecting brace/strap by way of the Achilles area which lengthens horizontally the full extent of the forward motion of the lower leg, and extends vertically to connect to the heel itself, pulling up on the heel to increase jumping power.

The standard ankle wrap long used by athletes in all sports is a triangular pattern extending horizontally across (or around) the ankle, then extending down from both sides and both ends of the ankle to under the heel/arch area then back up to connect at both the back and front of the ankle. It is completely interconnected to bind up the ankle and prevent injury. A different method of wrapping was tried by the present inventor. This method did not bind the ankle but rather created a pulling force upward on the heel. The wrap looked U-shaped, not triangular, as it extended from the shin to the Achilles area to the heel to the dorsum, with no direct connection between the shin and the dorsum or shin and heel. Jumping was easier and higher. However, after some use, the wrap would gradually pull down the leg losing its tension and most of its value, no matter how well the wrap had been taped.

The solution to the shin anchoring problem came with the conception of an inverted, steel angle brace (a shelf support brace) anchored to the sole of the shoe, then extending up to the top of the Achilles area where a pivot point (such as a pulley) is located to guide a cable from the shin horizontally to the Achilles area (so the force does not pull down at the shin), and then vertically to a soft sling directly under the heel itself, which is separate from the angle brace or shoe.

It is this (1) horizontal pulling and (2) separation of heel sling from the shoe, with an independent entity (the ground) which supports the shoe which supports the pulling force at the pulley on the angle brace that eliminates the problem of two or more forces working against each other and the two chief elements which make the current invention different from all those preceding. If Borden could eliminate the ankle hinge which creates the triangular binding similar to the conventional ankle wrap, the Borden invention might work except there would then be nothing to hold up the shin brace (it would pull down). Even if Borden's spring strap connected directly to the heel rather than to the heel socket, the triangular binding pattern would still be present due to the ankle hinge. Also, the pulling force would be minimal since it does not derive from the large, forward movement of the leg, but only from a slight movement of the Achilles area. The only embodiment of Borden which eliminates the triangular binding pattern is the coil spring pivot axis, but the previously mentioned forward motion of the rotating ankle joint going into the jump-ready position would still cause a binding problem, plus the jumping force is far too great for a spring of that size to control.

Detoro, U.S. Pat. No. 5,088,479, teaches a device which resembles the subject invention in appearance only. It serves a completely different purpose. In the present invention, the angle brace is claimed only in conjunction with the supporting of flexible braces or straps which are completely different from any straps of Detoro, which merely serve as attachments. In the present invention, the dorsum tension brace or strap 1) mimics the tendons underlying the arch which support the foot against collapse when weight is placed on the ball of the foot at the jump-ready position, thus allowing greater ease in heel movement upwards in relation to the ball, and 2) receives energy from the force of expansion of the dorsal foot due to the weight of the jumper. The brace or strap is flexible but not elastic and extends between its attachment to the foot in the dorsum area and its attachment separate from the foot in the Achilles area. The energy return helps overcome gravity going into the jump. Also, in the present invention, the dorsum tension brace does not fix the device to the foot. It attaches only to the rigid angle brace in the upper Achilles area. In Detoro, there are shown three dorsum straps which attach the sleeve 28 to the patient's foot at three velcro fastener areas 30. There is no direct connection (or pulling force) between the front of the foot and the Achilles area (either lower or upper). Therefore, there is no force pulling the foot into the desired obtuse angle, lift-off position.

The device of Mann et al., U.S. Pat. No. 4,954,871, is referred to as ribs 18 and 20 on each side of the foot within a mold, which is in an entirely different location than that of the present invention. The resulting orthosis of Mann et al. securely maintains the foot and leg in a slightly less than ninety degree angle, rigidity enhanced by the ribs. In the present invention, the foot has its normal full range of movement. In Mann et al. there is no attachment to the ribs by any straps similar to the dorsum tension brace of the present invention.

A further attempt at designing a device which would propel a user to greater jumping heights is what is shown within U.S. Pat. No. 4,941,273, issued Jul. 17, 1990, to Theodore S. Gross. In Gross, because there is no rigid support of the Gross strap, equivalent to the angle brace of the present invention, heel strike would actually shorten the distance between anchor points because of the cushiony heel which would lessen the tension. It appears that lift-off would cause tension due to bending of the foot at the ball area, but then it is too late as tension must occur going into the jump. Moreover, the "artificial tendon" of Gross will not work as a tendon because its forward anchoring point is in the shoe.

SUMMARY OF THE INVENTION

When jumping occurs, the human first must move into the jump-ready position. The at-rest position of the leg and the foot is with the foot being located at a substantially right angle to the longitudinal axis of the lower leg. When the individual moves into the jump-ready position, the lower leg of the individual moves forward which causes an acute angle to be produced between the longitudinal center axis of the lower leg and the longitudinal axis of the foot. Harnessing power from the forward leg movement can be done by connecting the shin area to the heel via the Achilles area causing upward pull on the heel. At this time the individual's downward weight movement also causes a slight spreading and lengthening of the foot which is unnoticeable except by close examination. This invention seeks to both limit this movement and harness energy provided by this movement. The individual then pushes off the ball of the foot at which time the foot will leave the ground or floor creating an obtuse angle between the lower leg and the foot in the lift-off position. The jumping assist system of the present invention is basically dormant during the time that the foot is in the at-rest position and during the time that the obtuse angle is created between the leg and the foot at lift-off. However, when the individual moves into the jump-ready position, a pulling force is applied to a tension brace which is located along the back of the lower leg to beneath the heel of the foot, with this tension brace being located parallel to the Achilles tendon. The upper end of the tension brace is connected by a strap to the front part or shin of the lower leg. The lower end of the brace is essentially fixed in position relative to the heel of the foot. When the lower leg extends forwardly, the distance between the shin and heel increases such that a stretching occurs along the length of the brace producing a pulling force so that at the time the jumping is initiated this pulling force causes the foot to snap with greater force from the jump-ready position to the lift-off position. The tension can be mostly an elastic system located separate from the shoe or it can be a cable system guided by a semi-rigid angle brace of spring steel type strength fixed to the sole of the shoe.

An objective of the present invention is to construct a jumping assist system comprising a one-piece "soft" version worn directly on the foot under the shoe which will assist the human in jumping. This objective is to be accomplished primarily by harnessing the force created by the weight of the human's body moving the leg forward at the shin and applying that force directly under the heel for increased upward lift and secondarily by controlling and harnessing energy from the flattening, lengthening and widening movement of the foot which occurs going into the jump when the foot contacts the floor momentarily under the individual's force of weight during forward and sideways motion.

DETAILED DESCRIPTION OF THE PREFERRED EMBODIMENT

Figure 1:
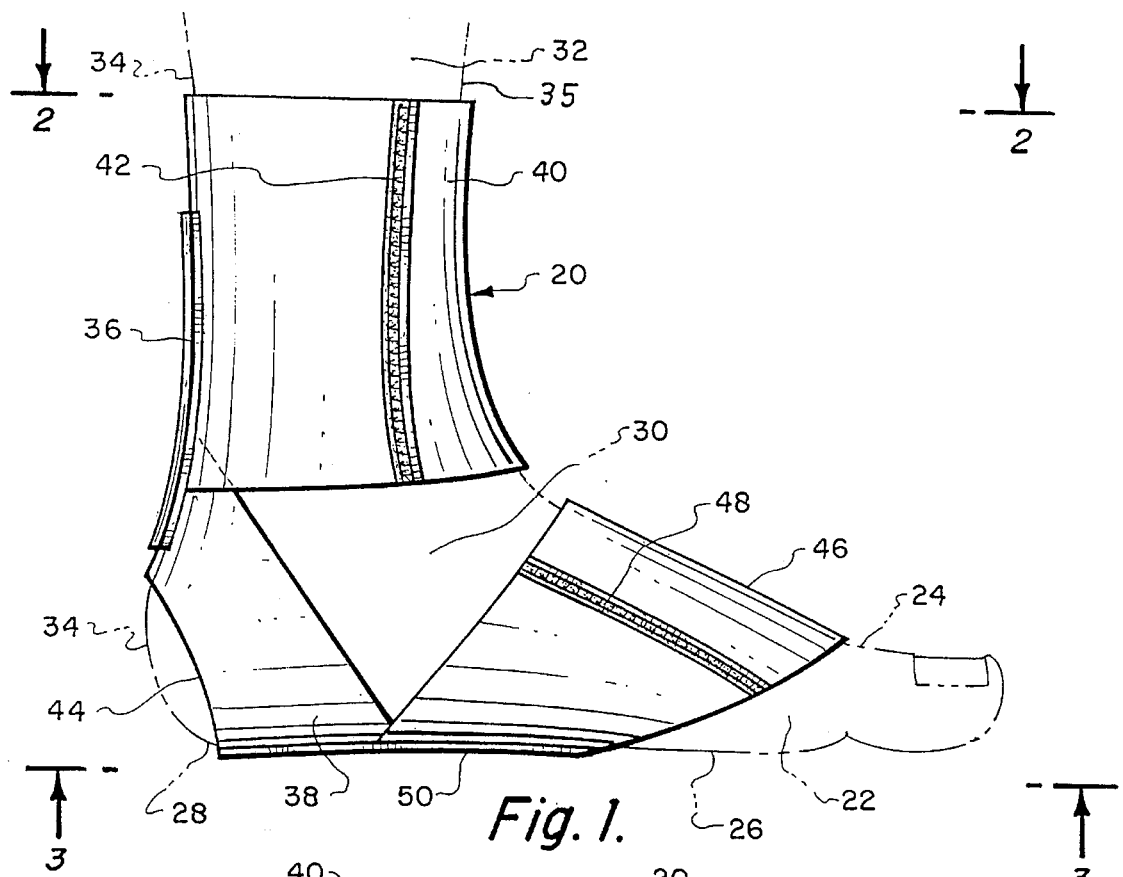
FIG. 1 is a side elevational view of the jumping assist system of the present invention showing the jumping assist system being mounted in conjunction with the lower leg and foot of a human.
Figure 2:
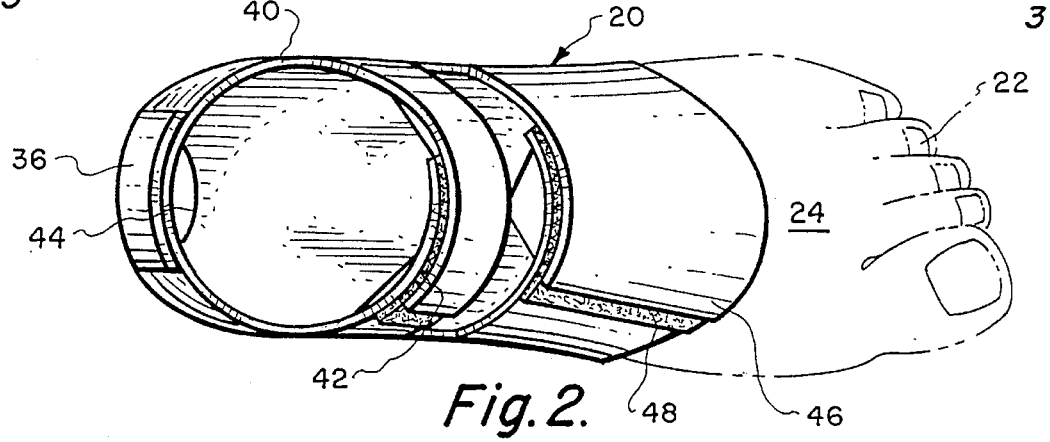
FIG. 2 is a top plan view of the system of FIG. 1 taken along line 2—2 of FIG. 1.
Figure 3:
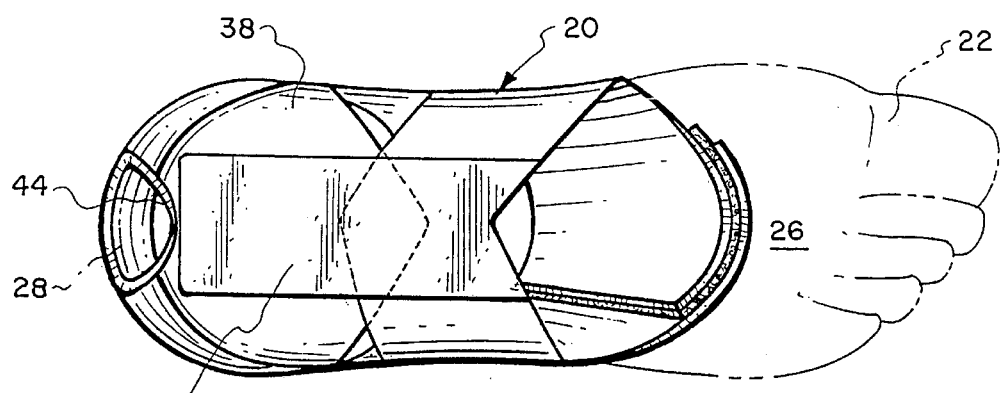
FIG. 3 is a bottom plan view of the first embodiment of the jumping assist system of the present invention taken along line 3—3 of FIG. 1.
Figure 4:
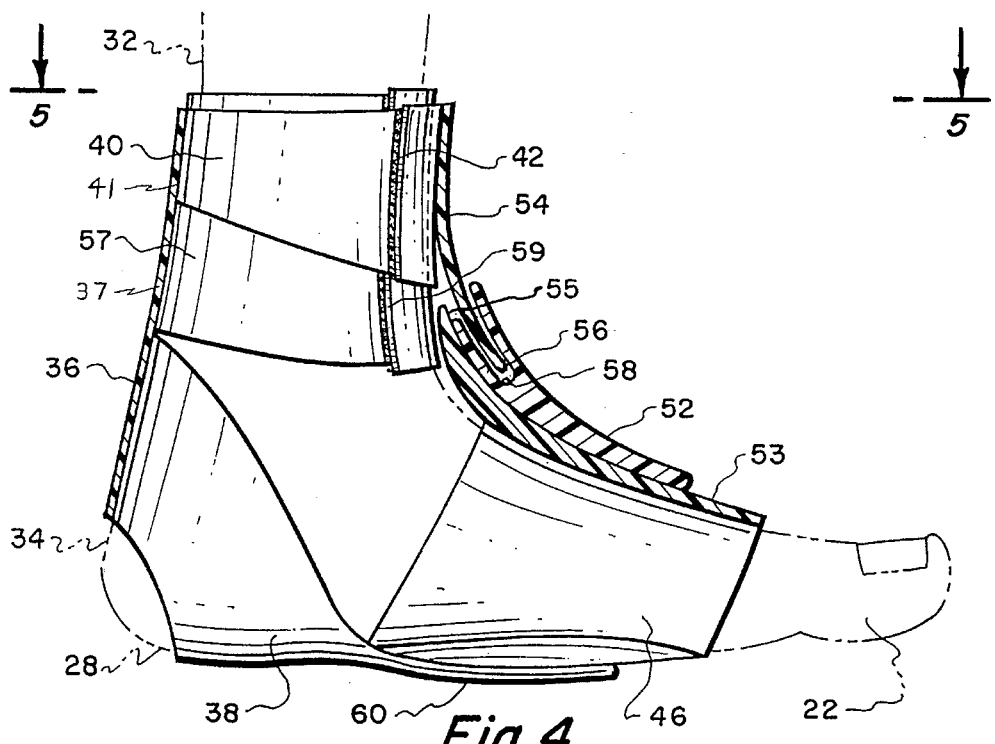
FIG. 4 is a modification of the jumping assist system of FIG. 1 showing the incorporation of a movement restricting brace device.
Figure 5:
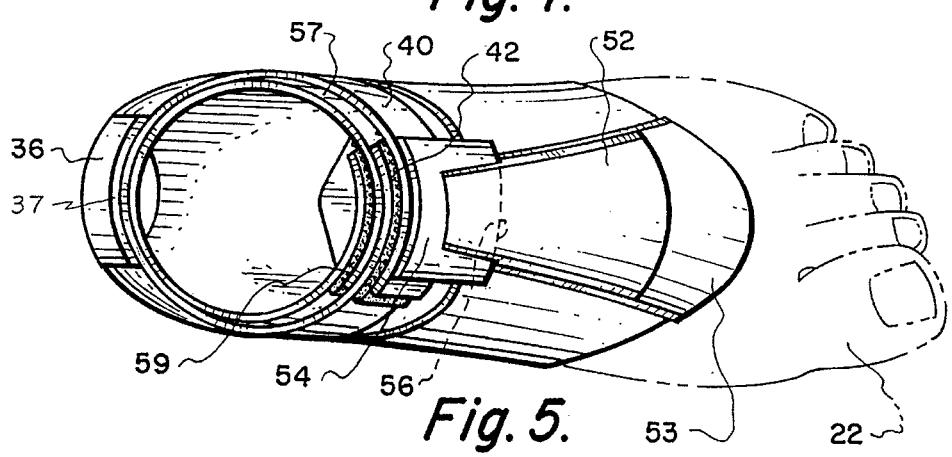
FIG. 5 is a top plan view showing more clearly the brace utilized in conjunction with FIG. 4 taken along line 5—5 of FIG. 4.

Referring particularly to the drawings, there is shown the first embodiment 20 of the jumping assist system of this invention. The jumping assist system 20 is shown mounted in conjunction with a human foot 22 which has a dorsum 24 which is in the metatarsal area of the foot 22. Foot 22 also includes a bottom surface which forwardly has a ball 26 and rearwardly a heel 28. Located upwardly of the heel 28 is an ankle joint 30. Located above the ankle joint 30 is the lower leg 32. The back edge of the lower leg 32, which extends to the heel 28 is defined as the Achilles area 34. The front edge of the lower leg 32 is defined as the shin 35.

Located directly adjacent and in alignment with the Achilles area 34 is an Archilles tension brace 36. This Archilles tension brace 36 includes a heel sling 38 which encompasses the heel 28. Fixedly secured to the upper end of the tension brace 36 is a lower leg strap 40. This strap 40 is to have overlapping ends which secure together by interlocking hook and eye pads forming a releasable fastener 42. The use of such releasable fasteners is deemed to be conventional and is conventionally marketed under the trade name of VELCRO. The use of such a fastener 42 is for the purpose of accommodating different sizes of lower legs 32 to thereby make the jumping assist system 20 usable in conjunction with different individuals.

It is to be noted that the heel sling 38 surrounds the heel 28 and has an enlarged opening 44 through which the heel 38 extends. The material of construction for the heel sling 38 could be leather or fabric. The remaining portion of the brace 36 includes a strip 37 that could be constructed of fabric or leather. This strip 37 is shown to be an inch to two inches wide and is basically located to be parallel to the Achilles tendon (not shown).

When the user proceeds to the jump-ready position, the lower leg 32 will move forwardly into the jump-ready position, with the anchoring point 41 of the tension brace 36 moving forwardly thus increasing the distance between the anchoring point at the lower leg strap 40 and the heel sling 38 thus exerting a force backward and downward on the lower leg strap 40, and upward on the heel sling 38 such that the opposing force on the lower leg strap 40 from the forward weight and motion of the body will help overcome resistance at the heel 38 due to gravity, thus pulling the heel 28 upward and increasing the propulsion of the jump.

To further assist in the application of the pulling force, there may be utilized a dorsum tension brace 46. The dorsum tension brace 46 is also to have ends which are to be secured together by a releasable fastener 48 which is basically similar to fastener 42. The dorsum tension brace 46 will be constructed of a fabric, leather or similar type of material similar to the lower leg strap 40. The dorsum tension brace 46 is fixedly secured underneath the ball 26 to a forward extension 50 which is located along the bottom of the foot 22 in between the ball 26 and the heel 28. The forward extension 50 will normally be constructed of a more rigid material and may be comprised of plastic, metal or may also include some type of a strong fabric. It is important to note that unlike a conventional ankle wrap which limits movement in all directions, there is no connection of straps between the shin 35 and dorsum 24.

When using the dorsum tension brace 46, the amount of the pulling force in a jumping procedure is magnified in two ways. One, within the Achilles tension brace 36, the dorsum tension brace 46 functions to keep the heel sling 38 in its proper place and prevents the heel sling 38 from moving rearwardly. Rearward movement of the heel sling 38 will diminish the amount of pulling force that is created within the Achilles tension brace 36. Two, depending on usage of materials and how such are connected, some force from the shin 35 to the heel 28 may extend further to the dorsum 24 causing a downward force on the dorsum 24 contributing to the desired rotational movement at the ankle joint 30.

It has been found that when jumping, there is a tendency for the lower leg strap 40 to lower along the front of the leg 32. There is also a tendency for the dorsum tension brace 46 to rise toward the lower leg strap 40. Straps 40 and 46 must remain in a fixed position in order for maximum pulling force on the heel to be attained. Therefore, in order to prevent such movement from occurring, there may be incorporated on the exterior most section of the dorsum tension brace 46 a movement restricting brace 52. This brace 52 will normally be constructed of a semi-rigid material such as plastic. Fixedly secured on the inside surface of the brace 52 is a padding layer 53. The padding layer 53 is fixedly mounted onto the dorsum tension brace 36. The padding layer 53 has an upward extension 55 which is to rest against a wrap-around padding 57 that is to be located against the leg of the user underneath lower leg strap 40. The free ends of the lower leg strap 40 are connected together by the releasable fastener 42. A similar fastener 59 connect together the ends of the padding layer 57.

Fixedly mounted on the exterior surface of the lower leg strap 40 is a position fixing brace 54. Position fixing brace 54 is constructed of the same material as movement restricting brace 52. The lower or leading edge 56 of the brace 54 rests within a channel or groove 58 formed with the brace 52. The upward extension of the padding 55 prevents the braces 52 and 54 from digging into the skin of the ankle as the user moves into the jump-ready position and brace 54 abuts brace 52.

It is also to be noticed that the heel sling 38 includes a forward extension 60 which rests within the arch area of the foot 22. The dorsum tension brace 46 is to be attached onto the forward extension 60. Normally, there will be located a padding type of material (not shown) in the area of the arch with this padding being fixed in position on the forward extension 60.

It is understood that position fixing braces 54 and 52 could be configured any number of ways, such as both partially encircling to the sides of the lower leg 32, or the brace 54 being as depicted but anchoring at the sides of the lower leg strap 40 to reduce pressure at the shin area. Braces 54 and 52 are to be free to move apart into the lift-off position with no resistance to each other, overlapping and abutting in such a way as to both impede the force of gravity pushing the leg forward at the optimum jump-ready position, thus increasing the transition speed from the jump-ready position to the lift off position, and maintain the position of the lower leg strap 40 and the dorsum tension brace 46 to provide maximum pulling force from the lower leg 32 to the heel 28. All padding could be accomplished by air filled bladders and augmented by air being forced from the bottom of the foot as the foot moves into the jump-ready position with the air being transferred to other areas requiring more protection. In fact, it is entirely possible that all the embodiments of this invention could be constructed of a plastic shoe more like the modern ski boot than the conventional basketball shoe, to provide easier means of attachment of braces to hold cables and straps in their proper positions, with all or most necessary padding accomplished by interlinking air chambers.

Figures 6, 6A:
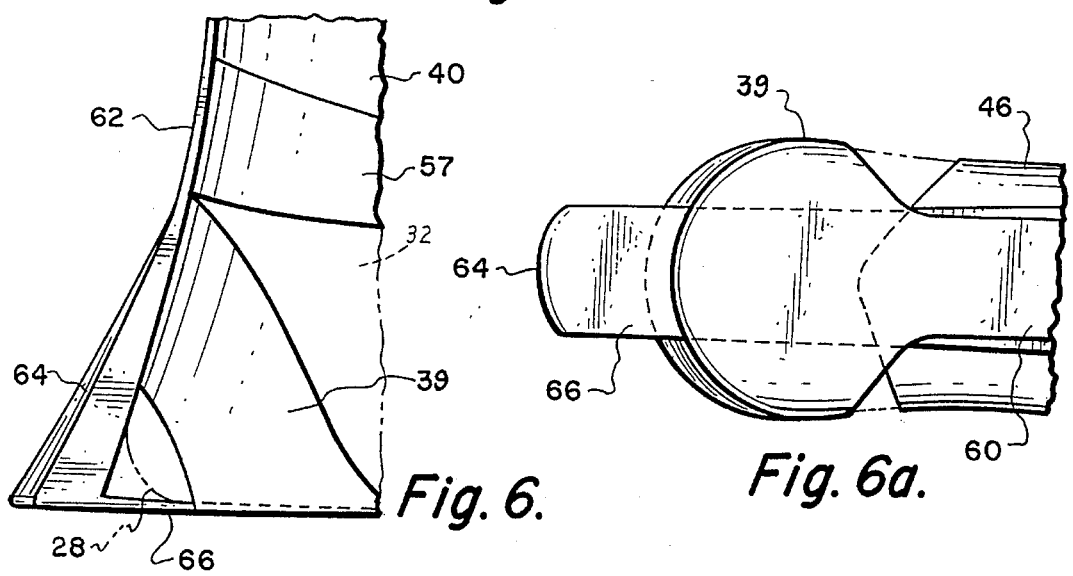
FIG. 6 is a segmental side elevational view of a modified form of the jumping assist system of this invention shown in FIGS. 1 to 5.
FIG. 6a is a segmental bottom plan view of the modified form of jumping assist system of FIG. 6.

Referring particularly to FIGS. 6 and 6a, there is shown a modification of the jumping assist system 20 of this invention in which the forward extension 60 includes a rearward horizontal extension 66. This rearward horizontal extension 66 would likely be constructed of spring steel or a strong plastic. The rearward horizontal extension 66 has been found to provide better leverage and smoother transition between forward leg movement and the resulting upward pulling force on the heel to the lift off position. Utilizing of the jumping assist system of FIGS. 6 and FIG. 6a, the friction of the jumping movement is reduced and jumping leverage is increased by extending in a rearward direction the rearward horizontal extension 66 some distance past the vertical plane of the heel 28 which is defined as the Achilles area 34. Also, the upward pulling force creates a pivot axis near the end of forward extension 60 under the heel 28 as the heel 28 becomes a fulcrum which causes a downward force at forward extension 60 helping to propel the foot into lift off from the ground due to the rotation of ankle joint 30. It has also been found that the rearward horizontal extension 66 provides cushion to the heel of an individual when walking, running or jumping independently of the Achilles tension brace 64.

It should be noted that the conventional arch support of the prior art is not of much value unless there is something supporting the arch support itself, which is the ground when standing flat footed. In jumping and running, however, the greatest gravity force that must be overcome occurs just after the heel leaves the ground, rendering conventional arch supports ineffective, even with an extremely rigid sole, because there is no pressure forcing the sole against the support during this stage of the jump. Part of the intention of the above described portion of the present invention, which we refer to more as the holding or supporting portion as opposed to the lifting portion (to be described further on) is to provide arch support during the time the user's weight is shifting to the ball of the foot.

To explain further how the arch support provided by the angle brace and dorsum tension brace improves jumping ability, the dorsum tension brace works in conjunction with those muscles in the sole of the foot (underlying the foot) which connect the heel to the ball, the action of these muscles being to hold or increase the curve of the transverse arch. These muscles hold the arch against spreading and collapsing under the individual's weight which allows the pulling force from the achilles area to carry through to the ball of the foot pulling the foot into an obtuse angle relative to the leg. The dorsum strap augments these muscles providing for less loss in energy during the transition between the jump-ready position and the lift-off position.

What is claimed is:

1. A system for use with a foot attached to a lower leg of a human at an ankle joint, the lower leg having a front edge defined as a shin and a back edge defined as an Achilles area which includes the Achilles tendon, the foot having a bottom surface with a ball located forwardly and a heel located rearwardly, the forward top portion of the foot being defined as the dorsum, the foot being pivotly movable at the ankle joint to form an acute angle in a jump ready position and then an obtuse angle in a lift off position, with the foot in said jump ready position the shin moves forwardly towards the dorsum which lengthens the Achilles tendon, the jumping height is increased the faster the Achilles tendon contracts pulling on the heel which pivots the foot at the ankle joint locating the foot in the lift off position, a jumping system for a human comprising:

an Achilles tension brace extending between the lower leg and the bottom surface of the heel, said Achilles tension brace being anchored to a sling at an anchoring point, said anchoring point being located in alignment with the back of the lower leg, as the lower leg moves forwardly into the jump ready position said anchoring point moves forwardly thus increasing the distance from the heel thus exerting a force backward and downward on the lower leg and upward on the heel such that the opposing force from the lower leg from the forward weight and motion of the body of the human will help overcome resistance at the heel due to gravity thus applying a pulling force pulling the heel upward increasing the propulsion of the jump;

a leg strap attached to the top of the Achilles brace;

a dorsum tension brace located at the dorsum and connecting with said Achilles tension brace at the bottom of the foot, said dorsum tension brace augments the pulling force by exerting a force downward against the dorsum tending to move the foot from said jump ready position to said lift off position as well as serving to hold said sling in a correct position thus increasing the pulling tension of said Achilles tension brace between the lower leg and the heel; and means for restricting downward movement of said Achilles tension brace at said anchoring point, means for restricting rearward movement of said dorsum tension brace by use of movement restricting braces mounted between said dorsum tension brace and said leg strap, said movement restricting braces being spaced from each other with the foot in said lift off position, said movement restricting braces abutting each other as the lower leg moves forwardly to said jump ready position.

2. The system as defined in claim 1 wherein:

said sling attaches to a substantially rigid section which extends forwardly from under the heel closely positioned against the arch of the foot and terminates at the ball.

3. The system as defined in claim 2 wherein:

said dorsum tension brace connecting to said substantially rigid section.

* * * * *